United States Patent [19]
Dickens et al.

[11] Patent Number: 5,468,770
[45] Date of Patent: Nov. 21, 1995

[54] GREEN LEAF VOLATILES AS INHIBITORS OF BARK BEETLE AGGREGATION PHEROMONES

[75] Inventors: Joseph C. Dickens, Starkville, Miss.;
Ronald F. Billings, Lufkin, Tex.;
Thomas L. Payne, Blacksburg, Va.

[73] Assignees: The United States of America as represented by the Secretary of Agriculture, Washington, D.C.; Texas A&M University System, College Station, Tex.

[21] Appl. No.: 168,839

[22] Filed: Dec. 17, 1993

Related U.S. Application Data

[62] Division of Ser. No. 662,601, Mar. 1, 1991, Pat. No. 5,273,996.

[51] Int. Cl.$^6$ .......................... A01N 31/00; A01N 31/02
[52] U.S. Cl. .................. 514/450; 514/690; 514/691; 514/724; 514/729; 514/738; 514/739; 514/763; 514/919; 424/195.1
[58] Field of Search .................... 514/724, 690, 514/763, 691, 450, 456, 739, 738, 729, 919; 424/195.1

[56] References Cited

U.S. PATENT DOCUMENTS 4,973,485  11/1990  Rich .......................................... 426/534

OTHER PUBLICATIONS

Fröhlich et al., "Volatile constituents of Curuba (*Passiflora mollissima*) Fruit," J. Agric. Food Chem., vol. 37(2), 1989, pp. 421–425.

Gergis et al., "Composition of the essential oils of *Sideritis cladestina* ssp cyllenea and *Sideritis sipylea*," J. Sci. Food Agric., vol. 47, 1989, pp. 501–507.

*Primary Examiner*—Allen J. Robinson
*Assistant Examiner*—John D. Pak
*Attorney, Agent, or Firm*—M. Howard Silverstein; Randall E. Deck; John D. Fado

[57] ABSTRACT

A composition for preventing or limiting the attack and infestation of trees by pine bark beetles, by inhibiting the response of the beetles to their aggregation pheromones. The composition comprises a green leaf volatile selected from six carbon alcohols, aldehydes, their derivatives such as acetates, and mixtures thereof. The green leaf volatile may be employed alone or in combination with an additional, known inhibitor of the pheromone response of the beetle.

13 Claims, No Drawings

GREEN LEAF VOLATILES AS INHIBITORS OF BARK BEETLE AGGREGATION PHEROMONES

This is a division of application Ser. No. 07/662,601, filed Mar. 1, 1991 now U.S. Pat. No. 5,273,996.

BACKGROUND OF THE INVENTION

1. Field of Invention

This invention relates to a method and composition for preventing or limiting the attack and infestation of trees by pine bark beetles, by effectively inhibiting the response of the beetles to their aggregation pheromones.

Bark beetles (Coleoptera:Scolytidae) are serious pests of forests throughout the world. Since most life processes such as feeding, mating, egg laying, and larval development occur safely beneath the bark of the host tree, control of the bark beetles is not possible using conventional control strategies, including use of insecticides.

2. Description of the Prior Art

Chemical signals play an important role in the orientation of insects to their host plants and conspecifics [Dickens and Payne, in *Handbook of Natural Pesticides: Methods Volume 1, Theory, Practice, and Detection*, ed. N. B. Mandava, p. 201 (1985)]. Compounds produced by feeding or calling males or females may attract both sexes as aggregation pheromones, or only the opposite sex as sex attractants. Chemical stimuli from plants may also be attractive to certain insects [Visser, *Entomol. Exp. Appl.* 20:275 (1976); Visser et al., *Entomol. Exp. Appl.* 24:538 (1978)]. In addition to the inherent attractancy of pheromones and certain plant odors, host plant odors, which may be unattractive alone, may enhance or synergize the attractancy of pheromones. For example, the aggregation pheromone of the southern pine beetle, *Dendroctonus frontalis* Zimm., is enhanced by the host monoterpene, α-pinene, which shows little inherent attractancy in field tests [Renwick et al., *Nature* 224:1222 (1969); Payne et al., *Environ. Entomol.* 7:578 (1978)].

Chemical communication by the guild of the southern pine bark beetles including *Dendroctonus frontalis* Zimm. (the southern pine beetle), *Ips avulsus* (the four-spined engraver), *Ips grandicollis* (the five-spined engraver), and *Ips calligraphus* (the six-spined engraver) is complicated and involves both beetle and host-tree compounds that can function in various behavioral roles [Vite et al., *Nature* 272:817 (1978); Birch et al., *J. Chem. Ecol.* 6:395 (1980); Svihra et al. *Naturwiss.* 67:518 (1980)]. Several investigations have documented the sequence of arrival and competitive interactions among *D. frontalis* and the three coinhabiting *Ips* species, and chemical signals have been found to play an important role in their temporal and spatial patterns of arrival on host trees and the intensity of attacks [Dixon et al., *J. Ga. Entomol. Soc.* 15:378 (1979); Birch et al., in *Current Topics in Forest Entomology*, ed. W. E. Waters, John Wiley & Sons, New York, p. 135 (1979); Birch et al., *J. Chem. Ecol.* 6:395 (1980); Svihra et al., ibid.].

Because bark beetles have such a complex chemical communication system, strategies aimed at disrupting this system could provide an effective and environmentally safe technique for control of the beetles and protection of the trees. Previous attempts to prevent or limit the attack and infestation of trees by bark beetles have included efforts to inhibit this communication between the beetles. Several compounds have demonstrated effectiveness in this regard, such as verbenone and endo-brevicomin, which have been identified as inhibitors of the aggregation pheromones of bark beetles. However, the cost of these compounds is high, limiting their use on a practical or large scale.

Green leaf volatiles are six carbon alcohols, aldehydes and their derivatives, e.g., acetates, which are produced by plants as a product of oxidation of surface lipids [Visser et al., *J. Chem. Ecol.* 5:13 (1979)]. These compounds appear ubiquitously in green plants and are thought to be released in characteristic ratios by different species. The odorous bouquet released from potato plants consists primarily of green leaf volatiles, and it was shown to be attractive to the Colorado beetle, *Leptinotarsa decemlineata* [Visser, *Entomol. Exp. Appl.* 20:275 (1976)]. This attractive effect could be masked or diminished by the addition of other green leaf volatiles [Visser et al., *Entomol. Exp. Appl.* 24:528 (1978)], as well as volatiles emitted from other non-host plant species [Thiery et al., *J. Chem. Ecol.* 13:1139 (1987)].

Recently, green leaf volatiles were shown to enhance responses of male and female boll weevils to their aggregation pheromone [Dickens, *Proc. XVIII Internat. Congr. Entomol. Abstr.* 213 (1988); Dickens, *Entomol. Exp. Appl.* 52:191 (1989)]. Subsequently, pheromone responses of the Mediterranean fruit fly, *Ceratitis capitata*, and the smaller European elm bark beetle, *Scolytus multistriatus*, were shown to be enhanced by green leaf volatiles [Dickens et al., *Naturwiss.* 77:29 (1990)].

SUMMARY OF THE INVENTION

We have now surprisingly discovered that members of the green leaf volatile complex, i.e., six carbon alcohols, aldehydes, their derivatives such as acetates, and mixtures thereof, are effective inhibitors of the pheromone responses of pine bark beetles, especially southern pine bark beetles. These green leaf volatiles may be employed in a composition, either alone or in combination with other known insect repellants or inhibitors of pheromone responses, for the protection of susceptible trees from attack or infestation, and the control of pine bark beetle populations.

In accordance with this discovery, it is an object of this invention to provide a composition for preventing or limiting the attack and infestation of trees by pine bark beetles, by inhibiting the response of the beetles to their aggregation pheromones.

Other objects and advantages of the invention will become obvious from the ensuing description.

DETAILED DESCRIPTION OF THE INVENTION

The lack of inexpensive and effective repellants or inhibitors of pheromone responses of pine bark beetles has limited efforts for the protection of trees from attack by these beetles. With the identification of compounds such as verbenone, endo-brevicomin and dipentene (a non-host terpene), which have been shown to be effective inhibitors and/or repellants, a tool has become available for the protection of susceptible trees. However, the high cost of these compounds has precluded their use on a practical scale.

According to this invention, there is provided a composition for controlling pine bark beetles which includes a green leaf volatile selected from six-carbon alcohols, aldehydes, their derivatives such as acetates, and mixtures thereof. The green leaf volatile may be employed alone or in combination with an additional, known inhibitor of the pheromone response of the beetle.

Surprisingly, unlike the response observed with a variety of other insects reported in the prior art, the green leaf volatiles act to inhibit the response of pine bark beetles to their aggregation pheromones.

An inhibitor of pheromone response is herein defined as a compound or compounds which disrupt the chemical communication between the insects such that their pheromone response is lessened (in comparison with the attractive response to pheromone alone). The effect of the inhibitor may be to either decrease the degree of insect attraction or aggregation in the vicinity of the inhibitor, or to repel the subject insects from the source or vicinity of the inhibitor.

Suitable green leaf volatiles contemplated by the invention include six carbon alcohols and aldehydes, their derivatives such as acetates, and mixtures thereof. Particularly preferred volatiles include but are not limited to: hexan-1-ol, trans-2-hexen-1-ol, cis-3-hexen-1-ol, hexanal, trans-2-hexenal, cis-3-hexenal, hexyl acetate, trans-2-hexenyl acetate and cis-3-hexenyl acetate.

As noted supra, additional known inhibitors of the pheromone response of the insects may optionally be used in combination with the green leaf volatiles. Suitable additional inhibitors include but are not limited to: verbenone, dipentene, endo-brevicomin, and mixtures thereof. It is understood that all enantiomers of the inhibitors are encompassed by this invention. These inhibitors may be present in the same or different composition than the green leaf volatiles.

The green leaf volatiles of the inventive composition are applied in conjunction with a suitable inert carrier or vehicle as known in the art. Alcohols, glycols, ketones, esters, aqueous mixtures, and solid carriers such as clays, cellulose, rubber, or synthetic polymers are illustrative of suitable carriers. The compositions may be applied in a variety of ways conventional in the art, such as in an exposed solution, or incorporated into a wick or other substrate. Of particular interest are those carriers allowing for controlled or slow release of the green leaf volatiles therefrom over an extended period of time, such as vials covered with a permeable septum or cap, sealed polyethylene bags, or liquid phase polymers subject to solidification on plant surfaces as after spraying.

The amount of the green leaf volatiles is selected to provide an effective inhibition of the pheromone response of the pine bark beetles. Effective concentrations of the green leaf volatiles in the composition may vary between about 0.1 and 99.9%. Suitable amounts and concentrations may be readily determined by the practitioner skilled in the art, and will of course vary with the size of the area to be protected; environmental conditions such as temperature, humidity, and wind conditions; the type of vehicle or carrier; and the amount of additional inhibitor used. In the event that additional inhibitors are used in conjunction with the green leaf volatiles, the amount thereof and its ratio to the green leaf volatile are also selected to provide an effective inhibition of the pheromone response of the beetles. Use of the green leaf volatiles in this combination allows for the dilution or use of lesser amounts of the more costly, previously known inhibitors while still retaining the desired inhibition of the beetles' response to their pheromones.

The compositions of the invention are effective in protecting trees from attack and/or infestation by pine bark beetles, especially members of southern pine bark beetle guild, including *Dendroctonus frontalis* Zimm. (the southern pine beetle), *Ips avulsus* (the four-spined engraver), *Ips grandicollis* (the five-spined engraver), and *Ips calligraphus* (the six-spined engraver). The composition may be employed to protect susceptible uninfected trees in areas of infestation or adjacent infested trees. In use, the composition is provided directly on, or adjacent to, or in the vicinity of the trees to be protected.

The following examples are provided to demonstrate the effectiveness of the green leaf volatiles of this invention to inhibit the response of various pine bark beetles to their aggregation pheromones. The examples are intended only to further illustrate the invention and are not intended to limit the scope of the invention which is defined by the claims.

EXAMPLE 1

Initial tests were conducted to examine the effect of the green leaf volatiles, hexan-1-ol and hexanal, on the attraction of *Denedroctonus frontalis* to its pheromone, frontalin, and the synergist, turpentine. Chemicals used in the field experiments, their purity and source were: racemic frontalin, 99% (Pherotech Inc., Vancouver, Canada); (−)-verbenone, 83% (Bedoukian Research Inc., Danbury, Conn.); hexan-1-ol, 98%; and hexanal, 99% (Aldrich Chemical Co., Milwaukee, Wis.). All field tests were conducted in east Texas forests.

Lindgren funnel traps containing the treatments shown in Table IA were located in a southern pine beetle infestation containing larvae, pupae, and brood adults. Traps were located in a circle with each trap 20–25 m from adjacent traps. Beetles were collected from the traps every two to three days, at which time the positions of the traps were rotated. Each treatment was tested in each position for at least one collection period. The data was analyzed by analysis of variance and Duncan's multiple range test [Ostle, *Statistics In Research*, The Iowa State University Press (1963)]. Slow release of the treatments from the traps was achieved by providing the treatments within dispensers as previously described [Billings, in *Integrated Control of Scolytid Bark Beetles*, ed. Payne et al., XVIII Internat. Congr. Entomol., Vancouver, Canada (1988); Rose et al., *Southwestern Entomol.* 6:1 (1981)], which dispensers were in 4 ml glass vials having a 2 mm hole in the cap and each containing two cigarette filters for adsorption of the components of the treatments. For those treatments involving two green leaf volatiles, a single dispenser of each was placed in each trap, while for all other treatments, two identical dispensers of the green leaf volatile were placed in each trap. The green leaf volatiles were not diluted prior to placement in the dispensers, about 5 ml of green leaf volatile being dispensed in each dispenser (about 10 ml per trap). Separate dispensers of frontalin (containing about 1 ml) and turpentine (about 250 ml) were also added to each trap. The elution rate of the treatments from these dispensers was relatively low, about 0.03 ml/day.

The results shown in Table IA demonstrate the inhibitory effect of the green leaf volatiles on the response of the beetles to their pheromone.

TABLE I

Attraction of *Dendroctonus frontalis* to Traps Baited with Racemic Frontalin + Turpentine and Various Combinations of (−)-Verbenone, Hexan-1-ol, and Hexanal Offered at Low (Tests A and B) and High (Test C) Elution Rates

| Treatment | Mean % of Total Insects Captured/ Replicate (n) | |
|---|---|---|
| A. Frontalin (F) + Turpentine (T) | 30.3a | (n = 5) |
| F + T + hexen-1-ol | 25.2a | |
| F + T + hexanal | 24.5a | |
| F + T + hexan-1-ol + hexanal | 18.8a | |
| Blank | 1.2b | |
| B. Frontalin (F) + Turpentine (T) | 16.7a | (n = 8) |
| F + T + hexan-ol-1 | 15.3ab | |
| F + T + hexan-1-ol + (−)-verbenone | 15.1ab | |
| F + T + (−)-verbenone | 15.1ab | |
| F + T + hexanal + (−)-verbenone | 13.8ab | |
| F + T + hexan-1-ol + hexanal | 13.2ab | |
| F + T + hexanal | 9.6b | |
| Blank | 1.1c | |
| C. Frontalin (F) + Turpentine (T) | 33.5a | (n = 5) |
| F + T + hexan-1-ol | 23.2b | |
| F + T + hexan-1-ol + hexanal | 19.8b | |
| F + T + hexanal | 16.2b | |
| F + T + (−)-verbenone | 5.4c | |

Means followed by different letters are significantly different (P < 0.05; Duncan's multiple range test) within each series of experiments.

A second series of tests was conducted in the same manner as the initial tests except using the treatments shown in Table IB to determine if the inhibitory effect of the green leaf volatiles was comparable to the inhibitory effect previously observed for (−)-verbenone.

A third series of experiments was subsequently conducted in the same manner as the initial tests, except using the treatments shown in Table IC and dispensers having a higher release rate of the treatment. Dispensers included a sponge saturated with 4–5 ml of the treatment and heat sealed within a 5 cm×10 cm polyethylene bag. The elution rate from the dispensers was relatively high, about 0.3 ml/dispenser/day. For those treatments involving two green leaf volatiles, a single dispenser of each was placed in each trap, while for all other treatments, two identical dispensers were placed in each trap.

EXAMPLE 2

A series of field tests was conducted to determine the effect of the green leaf volatiles, hexan-1-ol and hexanal, on the response of *Ips grandicollis* and *I. avulsus* to their aggregation pheromone mix, IPM (1% racemic ipsdienol+ 1% ipsenol+2% (S)-cis-verbenol, all obtained from Borregaard Industries, Sarpsborg, Norway). The tests were conducted in the same manner as the third series of tests in Example 1, except that Funnel-barrier traps were used [Rose et al., ibid.], and 6 ml of each green leaf volatile treatment was placed in each polyethylene bag, and about 10 mg of IPM was placed in a separate bag in each trap. The results shown in Tables II and III demonstrate the significant inhibitory effects of the green leaf volatiles on the response of both species to their aggregation pheromone.

TABLE II

Attraction Of *Ips grandicollis* to Traps Baited with Ips Pheromone Mix (1% Racemic Ipsdienol + 1% Ipsenol + 2% (S)-cis-Verbenol), and Combinations of Hexan-1-ol and Hexanol

| Treatment | Mean # of Insects (% of Total) Captured/ Replicate (n = 5) | |
|---|---|---|
| Ips pheromone mix (=IPM) | 48.6a | (32.4%) |
| IPM + hexan-1-ol | 48.2ab | (32.3%) |
| IPM + hexan-1-ol + hexanal | 27.6abc | (18.4%) |
| IRK + hexanal | 22.4cd | (14.9%) |
| Blank | 2.8d | (1.9%) |

Means followed by different letters are significantly different (P < 0.05; Duncan's multiple range test) within each series of experiments.

TABLE III

Attraction of *Ips avulsus* to Traps Baited with Ips Pheromone Mix (1% Racemic Ipsdienol + 1% Ipsenol + 2% (S)-cis-verbenol), and Combinations of Hexan-1-ol and Hexanal

| Treatment | Mean # of Insects (% of Total) Captured/ Replicate (n = 5) | |
|---|---|---|
| Ips pheromone mix (=IPM) | 31a | (41.8%) |
| IPM + hexan-1-ol | 18.8ab | (25/3%) |
| IPM + hexan-1-ol + hexanal | 14.2bc | (19.1%) |
| IPM + hexanal | 9.6bcd | (12.9%) |
| Blank | 0.6d | (1.0%) |

Means followed by different letters are significantly different (P < 0.05; Duncan's multiple range test) within each series of experiments.

EXAMPLE 3

Field tests were conducted to determine if a mixture of green leaf volatiles with additional known inhibitors (verbenone and/or dipentene) could be substituted for pure formulations of inhibitor (verbenone) as repellants for *Dendroctonus frontalis*. The tests were performed in the same manner as Example 1, except that the treatments shown in Table IV were used, and in the last treatment, two dispensers, each containing about 5 mg of a mixture of verbenone to hexan-1-ol to hexanal to dipentene of 1:1:1:1 (by volume), were placed in each tray. The results in Table IV demonstrate that the inhibitory properties of known inhibitors may be successfully maintained by dilution with less costly green leaf volatiles.

It is understood that the foregoing detailed description and Examples are given merely by way of illustration and that modification and variations may be made therein without departing from the spirit and scope of the invention.

TABLE IV

Attraction of *Dendroctonus frontalis* to Traps Baited with Its Pheromone Attractant + Host Synergist (i.e., Racemic Frontalin + Turpentine and Various Formulations of Verbenone, Hexan-1-ol, Hexanal, and Dipentene

| Treatment | Mean # of Insects (% of Total) Captured/ Replicate (n = 6) | |
|---|---|---|
| Frontalin (F) + Turpentine (T) | 226.2a | (40.2%) |

TABLE IV-continued

Attraction of *Dendroctonus frontalis* to
Traps Baited with Its Pheromone Attractant + Host Synergist
(i.e., Racemic Frontalin + Turpentine and Various
Formulations of Verbenone, Hexan-1-ol, Hexanal, and Dipentene

| Treatment | Mean # of Insects Captured/ Replicate (n = 6) | (% of Total) |
|---|---|---|
| F + T + 50%(+):50%(−)-verbenone | 101.5b | (18.1%) |
| F + T + 17%(+):83%(−)-verbenone | 96.5bc | (17.2%) |
| F + T + 34%(+):66%(−)-verbenone | 57.3bcd | (10.2%) |
| F + T + 69%(+):31%(−)-verbenone | 45.2cd | (8.1%) |
| F + T + [34%(+):66%(−)-verbenone + hexan-1-ol + hexanol + dipentene] | 35.3d | (6.3%) |

Means followed by different letters are significantly different ($P < 0.05$; Duncan's multiple range test) within each series of experiments.

We claim:

1. A composition for inhibiting or disrupting the response of pine bark beetles to their aggregation pheromones consisting essentially of an effective amount of: (1) a six carbon alcohol green leaf volatile effective as an inhibitor of the pheromone response of said pine bark beetles; and (2) an additional component effective as an inhibitor or repellant of the pheromone response of said pine bark beetles, wherein said additional component is selected from the group consisting of verbenone, dipentene, endo-brevicomin, and mixtures thereof.

2. A composition as described in claim 1, wherein said green leaf volatile is selected from the group consisting of hexan-1-ol, trans-2-hexen-1-ol, and cis-3-hexen-1-ol.

3. A composition as described in claim 1, further comprising an inert carrier.

4. A composition as described in claim 1 wherein said pine bark beetles are selected from the group consisting of *Dendroctonus frontalis* and *Ips avulsus*, and said six carbon alcohol green leaf volatile is effective as an inhibitor of the pheromone response of *Dendroctonus frontalis* and *Ips avulsus*.

5. A method for protecting pine trees from attack and infestation by pine bark beetles comprising: providing an effective amount of a composition comprising a six carbon alcohol green leaf volatile effective as an inhibitor of the pheromone response of said pine bark beetles in the vicinity of a pine tree to be protected.

6. A method as described in claim 5 further comprising an additional component effective as an inhibitor or repellant of the pheromone response of said pine bark beetle, said additional component being selected from the group consisting of verbenone, dipentene, endo-brevicomin, and mixtures thereof.

7. A method as described in claim 5 wherein said composition consists essentially of said green leaf volatile.

8. A method as described in claim 5, wherein said composition is provided on said tree to be protected.

9. A method as described in claim 5, wherein said green leaf volatile is selected from the group consisting of hexan-1-ol, trans-2-hexan-1-ol, and cis-3-hexen-1-ol.

10. A method as described in claim 5, wherein said composition further comprises an inert carrier.

11. A method as described in claim 5, wherein said composition is incorporated into an inert carrier.

12. A method as described in claim 11, wherein said inert carrier is effective to provide a controlled release of the green leaf volatile therefrom.

13. A method as described in claim 5 wherein said pine bark beetles are selected from the group consisting of *Dendroctonus frontalis* and *Ips avulsus*, and said six carbon alcohol green leaf volatile is effective as an inhibitor of the pheromone response of *Dendroctonus frontalis* and *Ips avulsus*.

* * * * *